United States Patent [19]

Levis et al.

[11] Patent Number: 5,210,412
[45] Date of Patent: May 11, 1993

[54] METHOD FOR ANALYZING AN ORGANIC SAMPLE

[75] Inventors: Robert J. Levis, Grosse Pointe Park; Louis J. Romano, Detroit, both of Mich.

[73] Assignee: Wayne State University, Detroit, Mich.

[21] Appl. No.: 648,282

[22] Filed: Jan. 31, 1991

[51] Int. Cl.$^5$ .................. B01D 59/44; H01J 49/40
[52] U.S. Cl. ............................ 250/288; 250/287; 250/282
[58] Field of Search ................ 250/288, 282, 423 P, 250/287

[56] References Cited

U.S. PATENT DOCUMENTS

| | | | |
|---|---|---|---|
| 4,220,414 | 9/1980 | Barringer | 356/317 |
| 4,598,577 | 7/1986 | Jowitt et al. | 73/23 |
| 4,678,326 | 7/1987 | Harjunmaa | 356/73 |
| 4,680,275 | 7/1987 | Wagner et al. | 436/518 |
| 4,681,859 | 7/1987 | Kramer | 436/501 |
| 4,731,532 | 3/1988 | Frey et al. | 250/287 |
| 4,751,190 | 6/1988 | Chipetta et al. | 436/546 |
| 4,757,141 | 7/1988 | Fung et al. | 536/27 |
| 4,760,258 | 7/1988 | Gast et al. | |
| 4,772,563 | 9/1988 | Evangelista et al. | 436/518 |
| 4,777,128 | 10/1988 | Lippa | 435/5 |
| 4,811,218 | 3/1989 | Hunkapiller et al. | 364/413.01 |
| 4,832,815 | 5/1989 | Cambara et al. | 204/299 R |
| 4,848,904 | 7/1989 | Sapp et al. | 356/319 |
| 4,852,017 | 7/1989 | Hunkapiller | 364/497 |
| 4,855,225 | 8/1989 | Fung et al. | 435/6 |
| 4,920,264 | 4/1990 | Becker | 250/288 |
| 4,927,265 | 5/1990 | Brownlee | 356/73 |
| 4,988,879 | 1/1991 | Zare et al. | 250/288 |
| 5,002,868 | 3/1991 | Jacobson et al. | 435/6 |
| 5,003,059 | 3/1991 | Brennan | 536/27 |
| 5,045,694 | 9/1991 | Beavis et al. | 250/288 |

FOREIGN PATENT DOCUMENTS 360676 3/1990 European Pat. Off. .

OTHER PUBLICATIONS

"Electrospray Ionization—Principles and Practice", Fenn, et al, *Mass Spectrometry Reviews*, 1990, 9, 37–70.

(List continued on next page.)

*Primary Examiner*—Bruce C. Anderson
*Attorney, Agent, or Firm*—Brooks & Kushman

[57] ABSTRACT

Described is a method and apparatus for analyzing an organic sample. In the preferred embodiment, this method and apparatus allows the determination of the base sequence of a nucleic acid by determining the molecular weights of the components of a biological sample. The method uses either a pre-existing chromophore or the covalent attachment of an ionizable chromophore to a biological sample followed by the vaporization of these molecules by exposure to an intense pulse of electromagnetic radiation in the presence of a matrix which strongly absorbs the radiation. The gaseous molecules are subsequently extracted into an evacuated ionization chamber and then exposed to electromagnetic radiation at a wavelength which specifically excites the chromophore covalently attached to the biological sample. The molecular weights of these ionized species are then determined by mass spectroscopic analysis. This method of molecular weight determination allows for a DNA sequencing method. Four samples of DNA molecules are prepared such that each is covalently linked to an ionizable chromophore and each is fragmented by a means which results in fragments within each of the four samples that terminate at a different one of the nucleotides A, C, G or T. Each of these four fragmented samples is subsequently introduced into the said apparatus in order to determine their molecular weights hence providing the strand length of the fragments. The data generated may be analyzed by high-speed computer, the four data sets correlated, and the sequence deduced.

38 Claims, 7 Drawing Sheets

OTHER PUBLICATIONS

"Pulsed High-Pressure Liquid Injection of Biological Molecules, etc.", Pang, et al, *Applied Spectroscopy*, vol. 42, No. 7, 1988, pp. 1200–1206.

"Volatilization of High Molecular Weight DNA by Pulsed Laser Ablation of Frozen Aqueous Solutions", Nelson, et al, *Science*, vol. 246, pp. 1585–1587, Dec. 22, 1989.

"Time-of-flight Mass Spectrometry: An Increasing Role in the Life Sciences", Robert J. Cotter, Biomedical & Environmental Mass Spectrometry, vol. 18, pp. 513–532 (1989).

Science/Technology, Human Genome Project Challenges Analytical Community Ward Worthy, C & EN Chicago, Sep. 1990.

Photon Resonance Mass Spectrometry John Wronka Spectroscopy, vol. 5, #3, 1987.

Biomolecules in the Gas Phase: Multiphoton Ionization Mass Spectrometry Jürgen Grotemeyer and Edward W. Schlag Acc. Chem. Res. vol. 22 Nov. 1989.

Secondary Ion Mass Spectrometry with Cesium Ion Primary Beam and Liquid Target Matrix for Analysis of Bioorganic Compounds, Aberth et al., Anal. Chem. vol. 54, Oct. 1982.

Nucleic Acid Related Compounds. 39. Efficient Conversions of 5-Iodo to 5-Alkynyl and Derived 5-Substituted Uracil Bases and Nucleosides Morris Robins Philip J. Barr, J. Org. Chem., vol. 48, 1983.

Forks and Combs and DNA: the Synthesis of Branched Oligodeoxyribonucleotides Thomas Horn and Mickey S. Urdea Nucleic Acid Research vol. 17, 1989.

Ultraviolet-Laser Desorption/Ionization Mass Spectrometry of Femtomolar Amounts of Large Proteins M. Karas, A. Ingendoh, U. Bahr and F. Hillenkamp Biomedical & Environmental Mass Spectr. vol. 18, 1989.

Lasers and Mass Spectrometry edited by David M. Lubman Oxford Univ. Press, 1990, pp. 353–382.

A System for Rapid DNA Sequencing with Fluorescent Chain-Terminating Dideoxynucleotides by James M. Prober et al., Science, vol. 238, Oct. 1987.

Mass Spectrometry by: A. L. Burlingame, D. S. Millington, D. L. Norwood and D. A. Russell Anal. Chem. 1990.

Cf-Plasma desorption mass spectrometry by: Bo Sundqvist and Ronald D. Macfarlane, Mass Spectr. Reviews 1985.

Mass Spectrometry and Its Use in Tandem with Laser Spectroscopy by: E. R. Grant and R. G. Cooks, Science, vol. 250, Oct.1990.

Enzymatic Synthesis of biotin-labeled polynucleotides: Novel Nucleic Acid Affinity Probes by: Pennina Langer, Alex Waldrop and David Ward Proc. Natl. Acad. Sci. USA, vol. 78, Nov. 1981.

Resonance Enhanced Multiphoton Ionization of Nucleosides by Using Pulsed-Laser Desorption in Supersonic Beam Mass Spectrometry by Liang Li and David M. Lubman; International J. Mass Spectr. & Ion Process 1989.

Biomolecules in the Gas Phase. III. Multiphoton Ionization Mass Spectra of Phenylthiohydantion Amino Acids and Free Amino Acids by Jurgen Grotemeyer, Klaus Walter, Ulrich Boesl and Edward W. Schlag, Int. Journ. of Mass Spectr. Ion Process, 1987.

"Molecular Weight Determination of Underivatized Oligodeoxyribonucleotides, etc.", Rapid Communications in Mass Spectrometry, vol. 4, No. 4, 1990.

"Electronic Spectroscopy of Small Tryptophan Peptides in Supersonic Molecular Beams", Cable, et al, Journal of the American Chemical Society, 1988, 110, pp. 7349–7355.

METHOD FOR ANALYZING AN ORGANIC SAMPLE

TECHNICAL FIELD

The present invention relates, in general, to a method capable of identifying or determining the molecular weights of organic samples and, in particular, relates to the use of this method to construct an automated apparatus that can determine the sequence of nucleic acids utilizing non-isotopic and non-electrophoretic techniques.

BACKGROUND ART

An important property of biological samples which often must be determined is their molecular weight. The most common method used to perform this measurement is to electrophorese the biomolecule through an acrylamide or agarose gel, visualize the position in the gel by staining or autoradiography, and determine the sizes by comparison to molecular weight standards of known sizes.

A related technology which uses similar sizing and detection techniques is DNA or RNA sequencing. DNA is a long thread-like macromolecule comprised of a chain of four deoxyribonucleotides which contain one of the four nitrogenous bases adenine (A), cytidine (C), guanine (G), or thymine (T). Similarly, RNA is composed of a long chain of ribonucleotides. The order of these nucleotides is the genetic code of the organism from which the DNA was isolated. The determination of this order is, therefore, a most important goal for scientists working in biological fields. Manual methods to sequence DNA involve either synthesis of new DNA in the presence of dideoxyribonucleotide terminators using as a template the DNA whose sequence needs to be determined or the degradation of the DNA to be sequenced using base-specific chemical treatments. In each case, a nested set of radioactively labelled DNA fragments are generated which represent the sequence of the DNA. For example, in the dideoxy method (Sanger, F. et al., (1977) PROC. NATL. ACAD. SCI. U.S.A., 74, 54635467), the template DNA, whose sequence is to be determined, is incubated with an oligonucleotide primer, four deoxyribonucleoside 5'-triphosphates (dATP, dCTP, dGTP and dTTP), and a DNA polymerase. The primer anneals to a specific complementary position in the template DNA that is defined by the order of the bases in the primer. The DNA polymerase then begins to catalyze DNA synthesis in the 5' to 3' direction by incorporating the deoxyribonucleoside 5'-triphosphate that is complementary to the next base in the template DNA. A complementary nucleotide is defined as one that follows the base-paring rules which require an A of one strand of a double-stranded DNA molecule always pairs with a T of the other strand and that a C of one strand always pairs with a G of the other strand.

In addition to the ability of DNA polymerases to incorporate normal nucleotides into the newly synthesized strand, many polymerases can also incorporate dideoxyribonucleoside 5'-triphosphates. Dideoxyribonucleotides are identical to deoxyribonucleotides except that they lack the 3'-hydroxy group on the ribose sugar. When these nucleotide analogs are incorporated into a growing DNA chain, synthesis terminates because the chain no longer bears the 3'-hydroxyl needed to add subsequent nucleotides. In the dideoxy sequencing method, four separate sequencing reactions are run, each containing one of the four dideoxyribonucleotides (each reaction also contains the four normal deoxyribonucleotides, one labeled with $^{32}P$ or $^{35}S$). Incorporation of the dideoxy analogs occurs occasionally and randomly in place of a normal nucleotide at complementary positions in the template so that each reaction generates a heterogeneous population of product DNA molecules each beginning with the primer (and thus sharing a common 5'-terminus) and each terminating with the dideoxynucleotide that was included in that reaction.

The radioactively labeled products from each of the four dideoxy sequencing reactions are denatured to separate the newly synthesized DNA from the template and then electrophoresed in adjacent lanes on a polyacrylamide gel such that the DNA product molecules are separated based on their chain length. The presence of a band in the gel represents the presence of the corresponding complementary nucleotide in the template at a specific distance from the primer. Comparison and analysis of the bands present in each of the four lanes allows the sequence of the template DNA to be deduced.

In the alternative chemical DNA sequencing method, chemicals that effect random partial cleavage of the DNA at G, G+A, C+T, and C are added in four individual reactions to a single-stranded DNA fragment containing a $^{32}P$ label at the 5' end. The resulting fragments are processed as in the dideoxy method to determine the DNA sequence. Maxam, A. and Gilbert, W. (1977) PROC. NATL. ACAD. SCI. U.S.A., 74, 560-564.

Automated DNA sequencing instruments based on the dideoxy method are described in U.S. Pat. Nos. and 4,811,218 and Prober et al., Science 16 October 1987, 238; pp. 336-341. Both of these systems require the incorporation of four fluorescent dyes into the dideoxy-terminated product DNA which are then run on a polyacrylamide gel. The discrete-length product molecules are detected near the bottom of the gel by their emitted florescence following excitation with a laser. In these automated systems, many more sequences can be analyzed per gel and the sequences determined accurately out to 500 bases or greater. Furthermore, data can be recorded faster since there is no manual gel reading step required. Finally, the automated sequencers use non-isotopic detection methods so there is not added costs associated with radioactive wasted disposal.

Although these instruments offer some advantages over manual methods, they still suffer from numerous drawbacks which are inherent in the use of a polyacrylamide gel to resolve the DNA fragments. For example, this method remains labor-intensive since a gel must be poured and disposed of for each sequencing run. Also, the accuracy of the sequencing can be impacted by artifacts generated by non-uniform gel matrix or even by a particular sequence as it electrophoreses down the gel. Furthermore, although more sequences can be determined on one gel that can be done manually, 10 to 12 hours are still required to obtain this data.

These problems associated with sequencing are minor when one is considering the generation of the sequence of a small genome, but they become monumental when contemplating sequencing the human genome, estimated to contain over 3 billion base pairs.

Mass spectral methods are well known. Pulsed mass spectroscopic methods, Burlingame, A. L. et al., (1990)

ANAL. CHEM., 62, 268R-303R (and references therein), such as time-of-flight (TOF) and Fourier transform ion-cyclotron-resonance mass spectroscopy (FTICR-MS), have the inherent ability to simultaneously analyze all of the components of a complex mixture in a single 200 millisecond experiment. The most significant feature of a mass spectroscopic-based method is that it does not require prior electrophoretic or chromatographic separation prior to analysis thus reducing the analysis time by at least three orders of magnitude.

A major obstacle, until now, for implementing mass spectroscopy for analysis of large biomolecules has been the lack of an appropriate interface between the water-based biological system and the high vacuum required for mass analysis. Prior studies have used techniques such as secondary ion mass spectroscopy, Aberth, W. et al., (1982) ANAL. CHEM., 54, 2029-2034, fast atom bombardment, Griffen, D. et al., (1989) BIOMED. & ENV. MASS SPECTROM., 17, 105, $^{252}$Cf plasma desorption, Sundqvist, B. et al., (1985) MASS SPECTROM, REV., 4, 421-460, electrospray, Fenn, J. B. et al., (1990) MASS SEPCTROM REVIEWS, 9, 37-70, and thermospray, Straub, K. et al., (1990) RAPID COMMUN. MASS SPECTROM, 4, 267-271, Pramanik, B. C. et al., (1989) ANAL. BIOCHEM., 176, 269-277, in an attempt to transport biomolecules from the solid phase to the gas phase. These methods suffer either from severe sample decomposition or multiple charging problems. Other obstacles for mass spectral DNA sequencing methods include: guaranteeing inadequate mass resolution at 30,000-200,000 AMU (100-500 base strands); accomplishing selective and efficient ionization of DNA strands; and avoiding multiple ionization and/or fragmentation of DNA strands.

Laser vaporization may be used for the desorption of biological molecules into the gas phase, Karas, M. et al., (1989) BIOMED. & ENV. MASS SPECTROM., 18, 841-843. Proteins with molecular weight approaching 175,000 daltons have been molecularly desorbed with this technique and detected using TOF methods, Karas, M. et al., (1989) BIOMED. & ENV. MASS SPECTROM., 18, 841-843. Recently, Cotter et al., (1990) RAPID COMMUN. MASS SPECTROM., 4, 99-102 have demonstrated matrix-assisted laser vaporization and high resolution TOF detection of oligodeoxyribonucleotides with mass up to 1797 Dalton (6 bases). In this case, the positive molecular ion peak was intense with no apparent strand cleavage. Autoradiographic studies by Williams et al. suggest that extremely long DNA strands, containing up to 1,200 nucleotides, (1989) SCIENCE, 246, 1585-1587, can be transported into the gas phase intact.

The resonance-enhanced multiphoton ionization is a tool for study of material based on exciting an atom or molecule with a laser through specific rovibronic states until the ionization energy is surpassed as shown graphically in FIG. 1.

Resonance-enhanced multiphoton ionization (REMPI), has been used to ionize many different biomolecules, including nucleotides and nucleosides, Li, L. et al., (1989) INT. JOURNAL OF MASS SPEC. & ION PROCESSES, 88, 197-210, peptides, amino acids, Grotemyer, J. et al., (1987) INT. J. MASS SPECTROM. ION PROCESSES, 78, 69-83, hormones, catecholamines, Pang, H. M. et al. (1988) APPL. SPECTROSCOPY, 42, 1200-1206, and purines, Li, L. et al., (1989) INT. JOURNAL OF MASS SPEC. & ION PROCESSES, 88, 197-210.

TOF mass spectrometry has detected proteins with masses approaching 175,000 AMU, Karas, M., Ingendoh, A., Bahr, U., Hillenkamp, F. (1989) BIOMED. & ENV. MASS SPECTROM., 18, 841-843. This would correspond to a DNA strand of approximately 530 bases long. Finally, the extremely high sensitivity a TOF mass spectrometer allows the detection of ultralow sample amounts in the sub-attomole range.

The difficulties of the prior art are overcome by the methods described herein to analyze an organic sample and/or to determine the base sequence of a nucleic acid.

It is an object of the present invention to use current sequencing technology with a mass spectral method to directly analyze the products of enzymatic DNA sequencing reactions.

It is the object of the present invention to solve inherent problems of the prior art described above using a combination of following techniques: (i) laser vaporization methods to desorb the liquid phase DNA strands into the gas phase; (ii) pulsed molecular beam nozzle techniques to transport the gas phase strands from a flowing helium atmosphere into the vacuum system; (iii) laser ionization methods to resonantly ionize a "tag" molecule on each DNA strand; and (iv) time-of-flight methods for high mass analysis.

It is an object of this invention to desorb biomolecules by mixing the sample of interest in an excess of a "matrix," or chromophore, which is specifically chosen to absorb light where the biomolecule does not. The chromophore absorbs the extremely high powered light ($10^6$-$10^9$ watts) that is presented in the short laser pulse (5ns).

It is an object of this invention to use this energy which is deposited in a short time so that all of the matrix and biomolecules are transported into the gas phase before thermal equilibrium can be attained.

It is an object of the present invention to place a single positive charge on the vaporized molecules using a technique called resonance-enhanced multiphoton ionization (REMPI). REMPI has been shown to be a very powerful tool for the analytical study of biological materials. The technique is based on selectively exciting an atom or molecule with a laser through specific vibronic states until the ionization energy is surpassed (FIG. 1).

It is an object of the present invention to place on each vaporized DNA molecule a single charge by selective ionization of a covalently attached chromophore or "tag." These charged ions are then detected using time-of-flight (TOF) mass spectrometry.

It is an object of the present invention to use the combination of a solution-phase laser vaporization method with the ability to measure high masses using a TOF mass spectrometer to provide a rapid (<5 sec) method to completely analyze all of the nested strands produced from a given enzymatic dideoxy sequencing reaction.

It is a further object of the present invention to determine the sequences of the bases of a nucleic acid sample. Prior techniques are extremely slow and are highly labor intensive.

It is also a further object to describe an improved apparatus for passing tagged biological samples from a vaporizing source to an apparatus which would permit the detection of the sequences of the components of a biological sample such as a nucleic acid such as DNA or RNA.

SUMMARY OF THE INVENTION

Described is a method analyzing an organic sample, comprising the steps of:
a) providing an organic sample in a medium which absorbs light;
b) vaporizing the sample and the medium into the gaseous state;
c) ionizing the vaporized sample; and
d) detecting the contents of the vaporized, ionized sample.

An apparatus is described for accomplishing this analysis comprising an optical source for generating electromagnetic radiation for the purpose of vaporizing the organic sample, an ionization chamber containing an optical source in which the vaporized sample is exposed to electromagnetic radiation that excites the sample and ionizes the sample, and a means to detect the ionized sample to analyze the sample. Most preferably, a mass spectrometer will be used to determine the molecular weights of the ionized sample. In the preferred embodiment, the mass spectrometer is of the time-of-flight type.

To use this apparatus for sequencing DNA or RNA, the sample to be sequenced is used as a template according to the dideoxy sequencing procedure employing in these enzymatic reactions either primers or dideoxyribonucleoside 5'-triphosphates that are covalently attached to a chromophore. The four enzymatic reactions products are then subjected individually to vaporization, ionization and mass analysis and the data correlated from each set to generate the sequence for each nucleic acid sample.

DETAILED DESCRIPTION OF THE INVENTION

Figure 1:
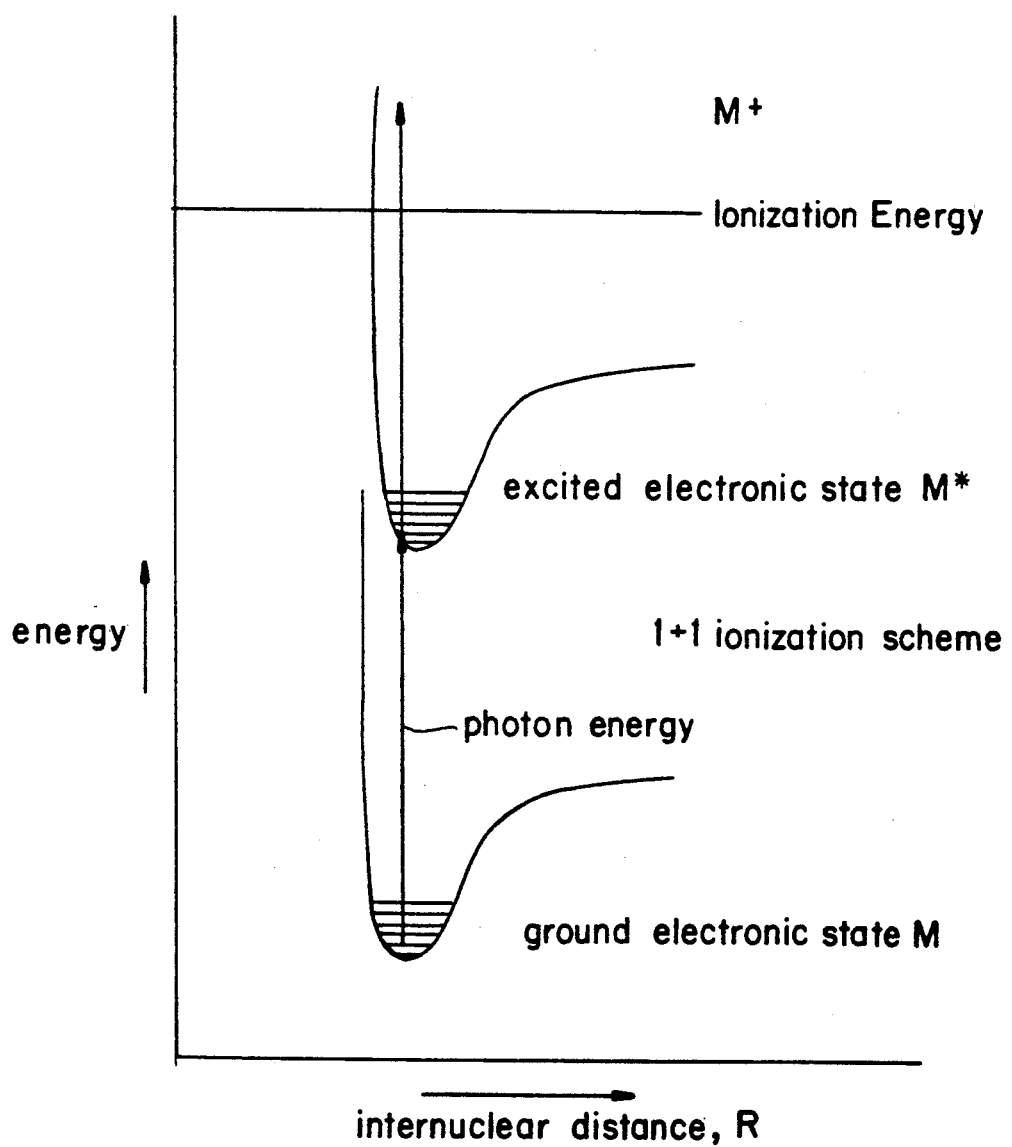
FIG. 1 shows a schematic view of a 2-photon resonance enhanced ionization experiment for a molecular species.

This invention includes a method for analyzing and identifying the components of an organic sample and an apparatus for accomplishing this method. In the preferred embodiment, the identification is through a determination of the molecular weights of these components and the preferred components are the products of a dideoxy sequencing reaction.

A feature of the invention, which uses laser desorption of biomolecules, is to mix the sample of interest into an excess of a "matrix" or chromophore, which is specifically chosen to absorb light where the biomolecule does not. It is believed that the chromophore absorbs the extremely high-powered light ($10^6$–$10^9$ watts) that is present in the short laser probe (5 ns). Possible chromophores includes nicotinic acid, sinapinc acid, ferulic acid, nitrobenzyl alcohol, benzene, diiodomethane, rhodamine G, and the like. This energy is deposited in such a short time that probably all of the matrix biomolecules are transported into the gas phase before thermal equilibrium can be attained. It has been shown that little or no degradation of thermally labile molecules results from this desorption technique.

If the sample does not contain a suitable chromophore for resonance enhanced multiphoton ionization, then a light-absorbing chromophore may be covalently linked to the sample. There are a large number of dye moieties which are appropriate for this ionization process. Suitable dyes include fluorescein and fluorescein derivatives, rhodamine and its derivatives, tetramethylrhodamine and its derivatives, sulforhodamine 101 (Texas red) and its derivatives, nitrobenzo-2-oxa-1-diazole, and the like. Derivatives of each of these dyes are commercially available from (Molecular Probes, Inc., Eugene, Oreg.) in forms that can be easily linked to appropriately activated biological or chemical samples. The most appropriate of the available derivatives of these dyes for the purpose of linking to biomolecules include: iodoacetamide, maleimide, isothiocyanate, and succinimidylcarboxylate. The appropriate functionality on the biomolecule to link to the first two in this series is SH, while the latter two require an $NH_2$ group present on the biological or chemical sample. For a listing of suitable dyes, see U.S. Pat. Nos. 4,821,218 and 4,855,225, hereby incorporated by reference.

There are a wide variety of standard procedures for chemically binding these types of chromophores to organic and biological molecules (see, for example, U.S. Pat. Nos. 4,821,218 and 4,855,225). Amine and thiol-containing nucleic acids can also be prepared and used to link to the appropriate reactive group on the dyes. Oligonucleotides are commercially available from many sources that contain either a reactive amine or thiol group at the 5' end (Clonetech, Palo Alto, Calif.). These are linked to the corresponding reactive groups on the dyes using standard procedures. There are also a number of commercially available oligonucleotides which are coupled to fluorescent dyes. For example, ABI (Foster City, Calif.) sells four oligonucleotides that are used in their automated DNA sequencer that are covalently linked to two fluorescein (fluorescein and 2',7'-dimethoxy-4,5-dichlorofluorescein) and two rhodamine (tetramethylrhodamine and rhodamine X) derivatives.

The dyes can also be covalently linked to a nucleotide. In the preferred embodiment where this method is used for DNA sequencing, these nucleotides are the four dideoxyribonucleotides containing the four bases A, C, G, and T. E. I. DuPont (Wilmington, Del.) sells the four dideoxynucleotides covalently attached to four closely related fluorescein dyes. ABI sells four dideoxynucleotides covalently attached to four rhodamine dyes. Also, there are several standard procedures by which each dideoxynucleotide can be coupled to a dye. For example, synthesis of the ddTTP derivative can be accomplished by converting ddUTP to 5-(3-amino)allyl-ddUTP by the method described by Langer, et al., (1981) PROC. NATL. ACAD. SCI. U.S.A., 78, 6633–6637. The cytidine analogue can be formed by converting dideoxyuridine to the 4-hexylamine derivative using a procedure similar to that described by Horn et al., (1989) NUCLEIC ACIDS RES., 17, 6959–6967, coupling to the NHS ester of a selected dye, followed by conversion to the triphosphate by one of several methods, Kozarich, J. W. et al., BIOCHEMISTRY, 12, 4458, Ruth, J. L. et al., (1981) MOL. PHARMOCOL., 20, 415. The dideoxyadenosine or guanosine derivatives might be similarly prepared by lithiation of the purine ring at C8 followed by alkylation with a suitably protected amine-containing alkylhalide, Barton, D. H. R. et al., (1979) TETRAHEDRON LETT., 279–280. Alternatively, the adenosine derivative could be prepared by iodination at C7 of the adenosine derivative, dideoxytubercidin, followed by coupling to N-trifluoroacetyl-propargylamine under Pd (0) catalysis, Robins, M. J. et al., (1983) J. ORG. CHEM., 48, 1854–1862.

These same dyes can also be covalently linked to proteins allowing detection and molecular weight determination of protein mixtures in biological samples. Unlike the nucleic acid modifications, proteins contain many reactive functional groups which will react with the preferred linking groups of the dye derivatives (isothiocyanate, succinimidylcarboxylate, iodoacetamide, and maleimide). For example, iodoacetates react predominantly with SH groups of free cysteines but may also react, if cysteines are absent, with methionines, histidines, or tyrosines. Maleimides are also primarily thiol-reactive but will also react with a amines at higher pH. Since many proteins do not have free thiols, the amine reactive functional groups, isothiocyanates and succinimidylcarboxylate, which react with free aliphatic amines are often the best choice for these types of coupling. Essentially, all known proteins have lysines and most have a free amino terminus. Therefore, these amine reactive dye derivatives are often the reagents of choice for protein modifications.

DESCRIPTION OF INSTRUMENT

Figure 2:
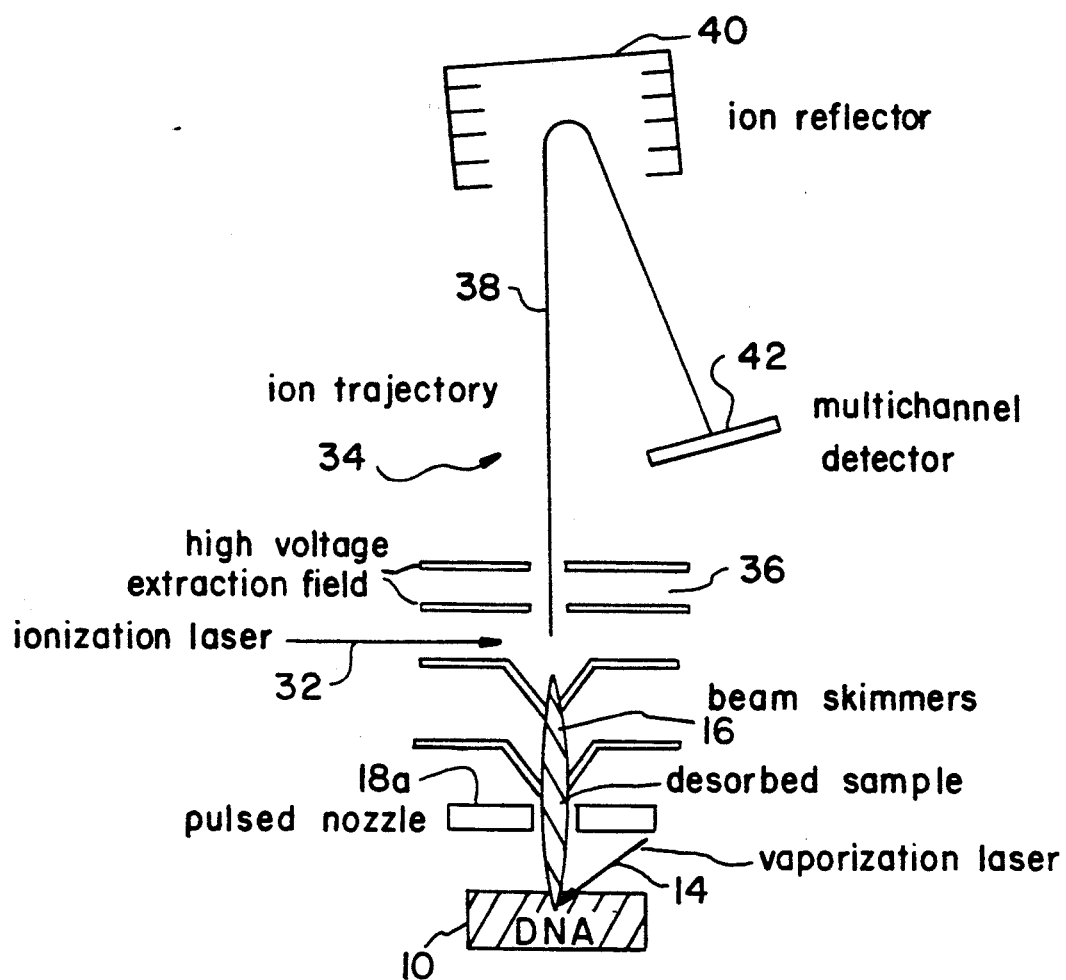
FIG. 2 is a schematic representation of the apparatus of the present invention.
Figure 3:
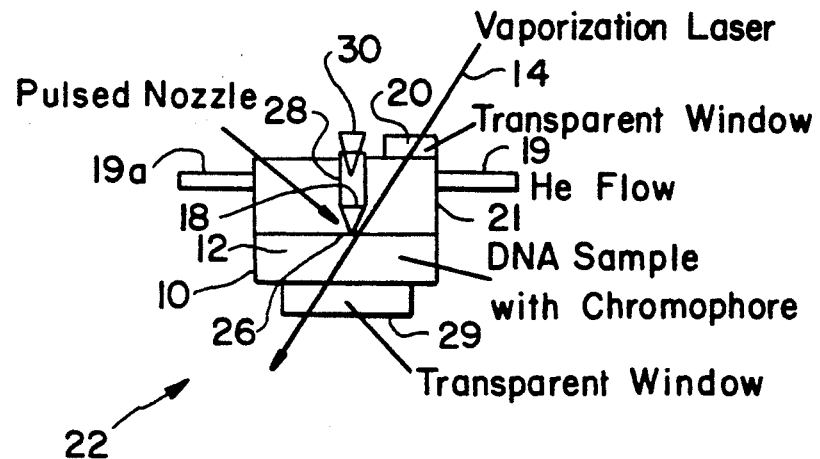
FIG. 3 is a schematic of an apparatus used to determine the internal energy distribution of laser vaporized materials.
Figure 4:
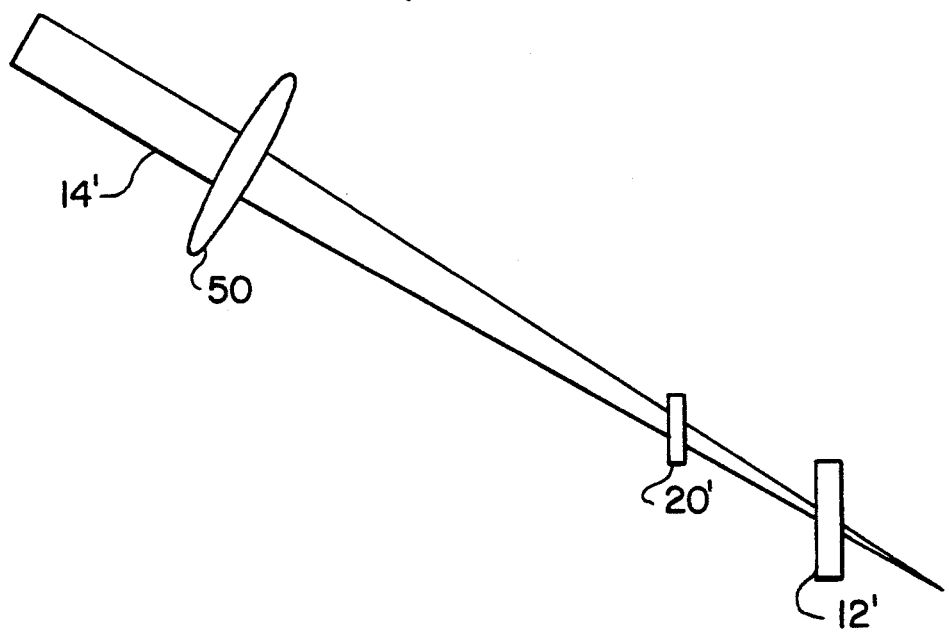
FIG. 4 is a schematic representation for the optical system for vaporization.
Figure 5:
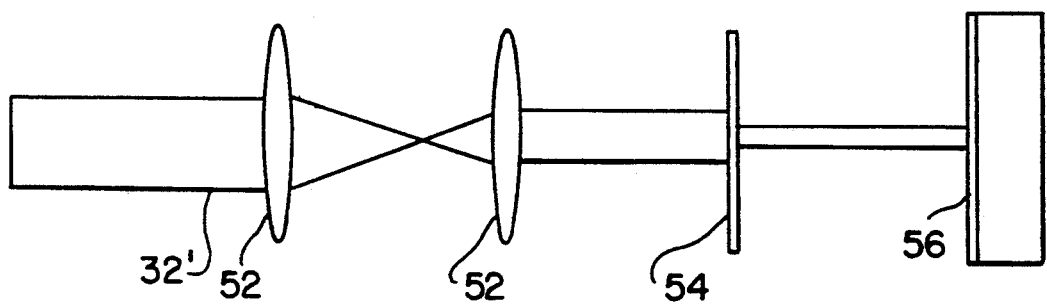
FIG. 5 is an optical system for REMPI.

Shown in FIGS. 2 and 3 is a schematic representation of a preferred embodiment of the apparatus which is made up of two sources of electromagnetic radiation—one for the vaporization step 14 and one for the ionization step 32, a vaporization chamber 21 and sample holder 10, a pulsed nozzle 18a, an ionization chamber generally at 33 and a mass spectrometer 34. While not specifically shown, a high efficiency pumping system would evacuate the low pressure chambers of this apparatus.

The vaporization chamber 21 as shown in FIG. 3 can be maintained at either vacuum or ambient pressure. In the preferred embodiment, the vaporization chamber 21 is maintained at ambient pressure. If the sample is a liquid, the sample holder will be oriented in a horizontal plane so that a liquid sample will not drip or run and will be situated such that it can be exposed to the electromagnetic radiation source. The sample holder is constructed from either polished 305 stainless steel or glass and is removable. It is affixed so that the sample can be reproducibly positioned in precisely the same location with respect to the pulsed nozzle. Alternatively, the sample could be dried to a solid by evacuation. Preferably, the sample of interest is mixed with an excess of a chromophore molecule prior to depositing onto the sample holder. The chromophore molecule is chosen to strongly absorb the laser light at a wavelength where the biological or chemical sample does not. In the preferred embodiment, the chromophore molecule is rhodamine 6G. The laser light strikes the sample and the chromophore molecule absorbs the light and is vaporized into the gas phase. The vaporized chromophore entrains the biological sample and carries it into the gas phase.

In the preferred embodiment, the source of the electromagnetic radiation to produce the vaporization is a laser, preferably neodinium yittrium aluminum garnet (Nd YAG) (a trademark of Quanta Ray of Mountainview, Ga.). This laser is operated in a mode which provides radiation at 532 nm up to 40 mW. The light is well columnated so as to provide high enough power to effect vaporization of the sample system. FIG. 4 shows the columnated light 14′ is directed through the optical system consisting of two pellin broca prisms (not shown) which remove unwanted frequencies of light. The unwanted light is directed to a beam dump for removal. The remaining light is then directed, first through an iris to restrict beam size and then through focusing optics 50 constructed from a nonabsorbing quartz S1 UV optical flat (1″×⅛″) into the vaporization cell to impinge onto the sample from above. The laser is operated in such a manner so as to produce an intense flash of electromagnetic radiation which will be absorbed by the vaporization matrix and not the sample. In the preferred embodiment, the light is absorbed by a dye molecule, e.g., rhodamine 6G.

In a preferred embodiment, once vaporized, the sample and chromophore are ejected into a helium atmosphere for subsequent processing. The helium injection and exhaust ports are positioned to maximize the flow of vaporized product toward the pulsed nozzle. The flow of helium is maintained using a He flow meter as supplied from Tylan Corporation. The output of the helium flow is connected to a pump via a metering valve. The pulsed valve is commercially available from Thermionics Laboratory, beam dynamics. The pulsed valve is positioned between 1 and 10 mm above the surface of the sample to be vaporized. The pulsed valve is timed to open 0.1 to 100 microseconds after the firing of the vaporization laser. The sample is extracted from the vaporization chamber into the ionization chamber. A potential is simultaneously applied to a 90% transmission grid to extract any ions which may have formed during the vaporization process and survived the transit through the pulsed nozzle.

Once the sample has entered the vacuum chamber a second intense burst of electromagnetic radiation is delivered into the apparatus from an excimer or YAG laser source. In the preferred embodiment, the ionizing radiation is at 308 mm. As shown in FIG. 5, this beam is developed using the following optical components. The beam 32′ is directed through a telescoping cylindrical lens 52 to shape the beam into a compact pulse. The beam is then passed through slits 54 to define the final shape of about a 1 mm×5 mm ribbon. The beam is then directed through a quartz window 56 into the vacuum chamber. In the vacuum chamber, the light intersects the beam of sample and dye molecules at a 90 degree angle. The sample molecules absorb the radiation and are ionized by resonant multiphoton processes.

The "tag" molecule in this mass spectral technique will perform a role analogous to the fluorescent tag employed in other automated electrophoretic DNA sequencing techniques. In the mass spectral technique, the "tag" will enable the detection of the DNA components by allowing the placement of precisely one unit of positive charge per DNA strand, permitting an exact determination of molecular weight or strand length. Single ionization of each strand will greatly simplify the appearance of mass spectrum of mixtures of DNA strands.

For a desirable REMPI tag for mass spectral analysis of DNA strand, it is most desirable that the molecule have an adsorption band greater than 300 nm (where DNA weakly absorbs). Secondly, the molecule should have excited states which allow resonant ionization. Lastly, the molecule should be chemically attachable to the DNA strand during the enzymatic reaction. Utilizing a tetramethylrhodamine chromophore, it is believed that the solution phase electron excitations may be centered around approximately 350 nm, 250 nm, and 200 nm for similar compounds. It is also desirable that the tag dye molecule be positioned at least 8 atoms and possible up to 29 atoms away from the DNA strands, depending upon the length of the linker arm that is chosen.

The ionized sample is then extracted by a three kilovolt potential applied to a 95% transmission grid which is 10 cm from the plane of the ionizing radiation. The ions formed in the electromagnetic pulse are then extracted into a mass spectrometer. In the preferred embodiment, the mass analysis system is of the time-of-flight type, such as a Bruker TOF 1 (Bruker Instruments, Inc. of Billerica, Mass.). This system has been developed to operate at 30 Hz, with a very large sample depth (128K) and high resolution (16 bit). This system is complete in terms of control electronics and also contains all of the ultra high vacuum pumping systems that will be required for the ionization chamber.

METHOD OF OPERATION

The apparatus of the present invention can be used to analyze biological or chemical samples generated from any one of a number of sources. For example, it is possible to analyze blood samples for the presence of various metabolites or proteins or even modified proteins. However, in the preferred embodiment, this instrument will be used to sequence DNA.

The DNA samples to be sequenced are processed according to the Sanger dideoxy sequencing method described above. These reactions are run with the light absorbing chromophore linked to either the primer or the dideoxyribonucleotides. Each of the four enzymatic reactions containing the dideoxy-terminated product DNA covalently linked to a light-absorbing chromophore are then mixed with an excess (e.g., 10–100,000 fold by weight excess) of rhodamine 6G and each of the four mixtures are placed individually into sample holder 9. In the case where the sample is analyzed in the solid phase, the water is removed by evaporation. In the case where the sample is analyzed as a liquid, the sample holder is placed directly into the vaporization chamber 21. The sample is then exposed to a 1-100 MW pulse from the laser at 532 nm which vaporizes the rhodamine 6G, and via entrainment, the biological sample. This vaporized material is extracted through the pulsed nozzle by the flowing helium stream, ionized by a 1 MW pulse from the eximer laser, and extracted by the three kilovolt potential applied to the 90% transmission grid into the time-of flight mass spectrometer. The molecular weights of the ions detected by the mass spectrometer are recorded. Then this entire process is repeated in sequence for the remaining three dideoxy sequencing reactions, the results from the four samples correlated, and the DNA sequence deduced as is done with manual or other automated sequencing methods.

Those skilled in the art will understand that there are many variations of the above apparatus and method that fall within the purview of this invention. For example, different chromophores could be used for the vaporization or ionization processes as could different sources of electromagnetic radiation. The sample may need to be pre-treated by various procedures to increase sensitivity levels, such as for example, removing the template DNA, removing the nucleotides, removing the protein prior to analysis. Furthermore, the sample holder and vaporization chamber could be modified so as to accept multiple samples by the addition of a movable stage that would bring each of the various samples into register for the vaporization step.

The sequencing method described here has numerous advantages over currently available or proposed approaches. First, it does not require that DNA sequencing products be run on a polyacrylamide gel. This component of manual or automated DNA sequencing is the most labor-intensive and time-consuming portion of DNA sequencing. Second, this method does not require the use of a radioisotope. Both this and the prior point should significantly reduce the expense currently associated with sequencing by reducing labor, chemical, and disposal costs. However, it may be possible, because of the potentially enhanced sensitivity of this method, to substantially reduce the level of template and enzyme used in the dideoxy sequencing reaction. For example, use of 1/10th the amount of DNA polymerase, template, primer and nucleotides would substantially reduce operating costs. Third, the throughput that can be expected for this instrument may be 1000 times, or more, that obtained from currently available automated sequencers. An important consideration is that the technology described here can be easily automated for repeated sample analysis. Since the mass analysis can be obtained very rapidly, a conservative estimate for the time involved in generating a single DNA sequence is certainly less than one minute, and should be as little as a few seconds. Thus, an instrument running continuously might conceivably be able to sequence well above a million bases per day.

In FIG. 3, the aqueous sample 12 is placed in a holder 10 and is subjected to the vaporizing laser depicted as 14. The desorbed sample 16 flows through a pulsed nozzle 18, best shown in FIG. 3. The vaporization laser 14 passes through the transparent window 20 at the top of the apparatus 22 that holds the pulsing nozzle 18. The laser beam passes through the transparent window 24 at the bottom of the apparatus 22 of FIG. 2.

The schematic of FIG. 2 shows the pulse nozzle at 18a. The purpose of the pulsed nozzle is to extract the gaseous sample resulting from the vaporization of the sample by the laser into the remaining apparatus as depicted in FIG. 2. The gas enters into the bottom of the pulse nozzle at reference numeral 26 passing through chamber 28 and out the upper portion 30 of the pulse nozzle. The gaseous sample from the vaporization laser 14 passes through the pulse nozzle together with the carrier gas helium, which enters vaporized chamber 21 through inlets 19 and 19a. Because the vaporized sample has the chromophore tag as a portion of the vaporized molecule, that chromophore tag can be excited by the ionization laser 32. The ionization laser causes the vaporized product to be ionized and the gaseous sample is then entered into or passes into the mass spectrometer generally depicted as 34 in FIG. 2.

In FIG. 2, the ionized molecules in the components of the DNA strand passes from the ionization laser into the mass spectrometer. The molecule is subjected to a high voltage extraction field 36 which excites and accelerates the mass of the component of the DNA strand which is shown as the ion trajectory 38. The ion deflector 40 and the multichannel detector 42 permit the movement of the individual strands through the mass spectroscopy equipment. The variations in the mass of the charged molecules allows an analysis of their mass and thereby determining the sequencing of the DNA.

The apparatus described herein has not been used previously to make determinations of the molecular weights of biological samples. Because of the uniqueness of the apparatus, unique materials are prepared by virtue of the ionization occurring by the ionization laser 32 after the DNA sample has been vaporized. It is because of this unique difference that the ionized molecules have enhanced capability of being detected more accurately and sensitively through the mass spec equipment. It is believed that these ionized molecules have not been described previously.

EXAMPLE 1

This example employs laser vaporization to produce DNA strands in the gas phase. This is followed by a laser ionization to place one positive charge on each DNA strand. The singly charged DNA strands are then detected to determine the mass of the DNA strand.

The findings comprise two results. The first is that a rhodamine dye molecule can be resonantly ionized even after covalently attaching the molecule to a DNA nucleotide. The second finding is that laser vaporization of a 17 base DNA strand can be performed without breaking any bonds within the DNA molecule. The combination of these two findings results in molecular desorption, molecular ionization and mass spectral detection of DNA strands resulting from a sequencing reaction.

Figure 6:
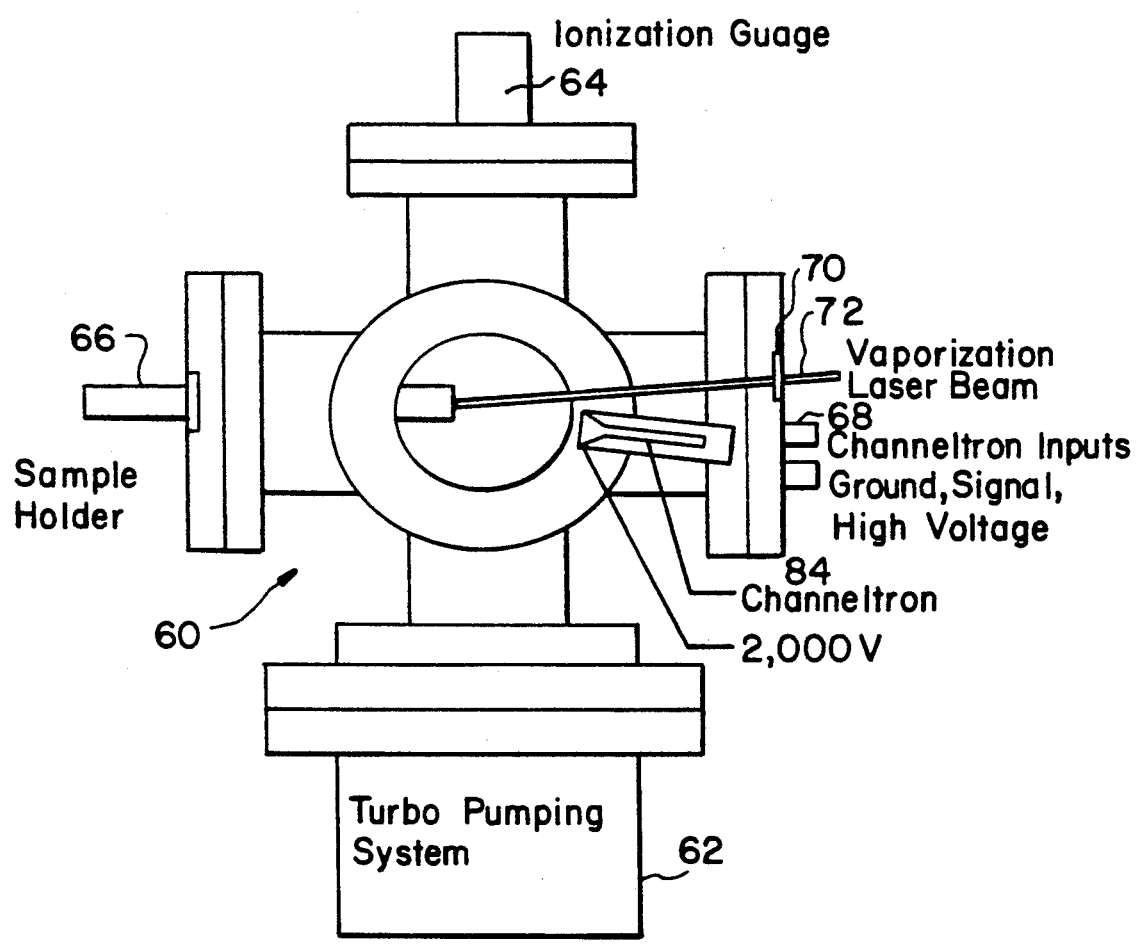
FIG. 6 is a side view of the prototype apparatus of the present invention.
Figure 7:
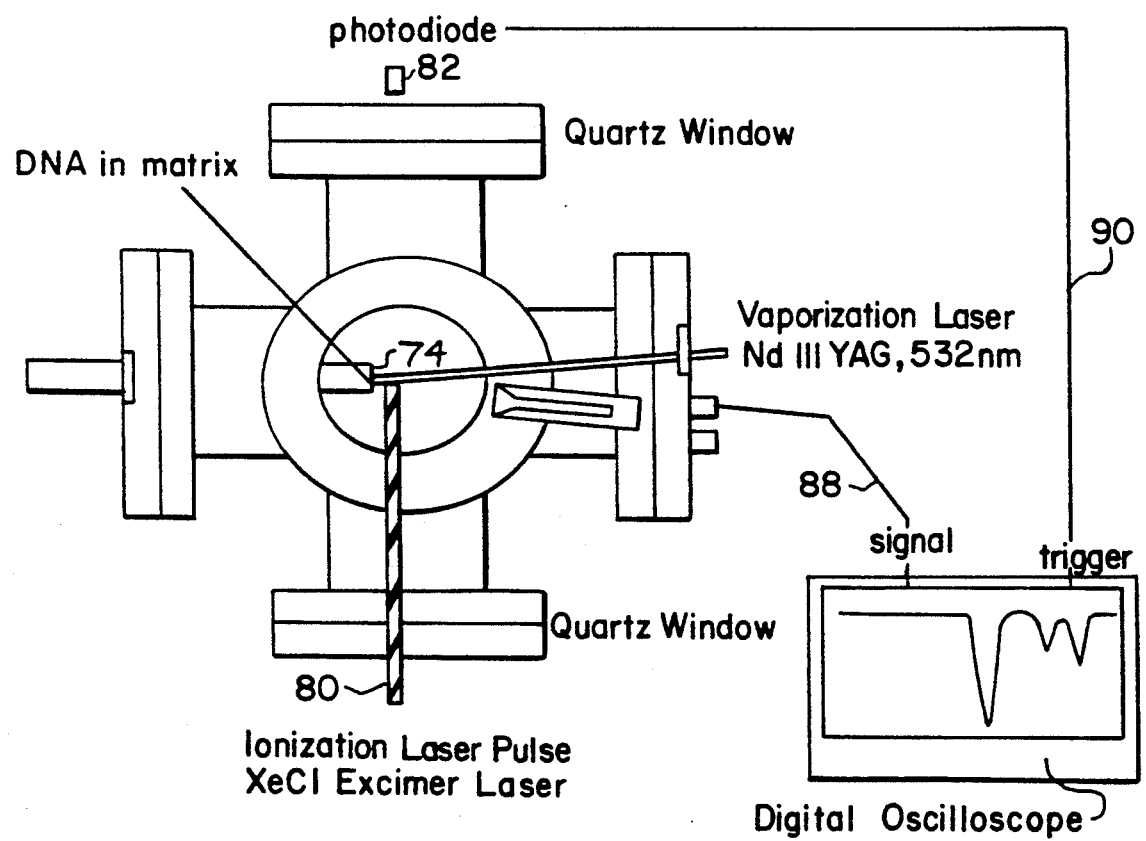
FIG. 7 is a top view of the prototype apparatus of FIG. 6.

The experiments were performed in the prototype sequencing chamber shown in FIGS. 6–7. The chamber consists of a standard six-way cross 60 pumped by a 400 l/s turbo pump 62. Two opposing flanges have quartz windows to allow the passage of the ionization laser. The top flange houses either an ionization gauge 64 or a view port. The remaining two opposing flanges house the sample positioning system 66 and ion detection system 68, respectively. The flange which houses the sample detection system has a "1" diameter quartz window 70 to allow the passage of the vaporization laser beam 72.

The DNA sample mixture 74 is spotted onto a glass coverslip which is attached to the end of the stainless steel sample positioner. The mixture of laser dye and tagged DNA sample is allowed to dry into a solid thin film on the coverslip 74. The sample is then loaded into the vacuum chamber and pumped to a pressure of approximately $5 \times 10^{-6}$ torr.

In both experiments described below, the vaporization laser strikes the thin film at an angle of approximately 5 degrees from the surface normal. The vaporization laser is the second harmonic of a Nd YAG III laser, (532 nm, 6ns pulse length, variable power). The YAG laser is equipped with gaussian optics so that the photon density within the beam is approximately constant across the diameter of the beam. The diameter of the vaporization laser beam is irised to 2 mm. The fluence of the beam ranges between 10 and 80 mJ/cm$^2$ as measured by a power meter (not shown). The sample positioning system is rotatable so that fresh sample can be continuously brought into the area of vaporization if necessary.

The multiphoton ionization laser 80, a 308 nm photon and 15ns pulse length, passes parallel to the plane of the thin film at a distance of 7 mm from the surface. The beam is irised and passed through 1 mm slits. The beam shape of the ionization laser 80 is a ribbon with dimensions 1 mm $\times$ 7 mm. For the experiments requiring ionization of the DNA sample, the excimer laser is triggered to fire at a time of 12 microseconds after the vaporization laser 14 hits the target. The pulse of photons from the ionization laser 80 is detected using a photodiode 82. The signal from this photodiode defines time=zero for the time-of-flight measurement.

The multiphoton ionization experiments were performed with an extraction voltage of 2 KeV over an extraction distance of 45 mm. The Galileo Channeltron 84 model 4680 to sample distance was 52 mm. The field lines in this chamber were not clearly defined. The approximate acceleration voltage was empirically found to be 1000 V. This was done by inserting a copper grid adjacent to the sample surface. The arrival time for the laser vaporized Cu ions was used to calibrate the mass scale for the time-of-flight system. The arrival time of a given ion is related to the ions mass by solving for time in a constant acceleration field:

$$X = \tfrac{1}{2} A t^2$$

where X=distance, 0.045 m; A=acceleration=force/-mass=1000 V/ 0.045 m mass; t=time of arrival in seconds. Solving for arrival time gives $$time = ((2 \times X^2 \times mass\ of\ ion)/V)^{\tfrac{1}{2}}$$

MULTIPHOTON IONIZATION OF TAGGED DNA

The aim of these experiments was to probe the possibility of ionizing a DNA sample by ionizing a dye molecule covalently bound to the DNA.

Figure 8:
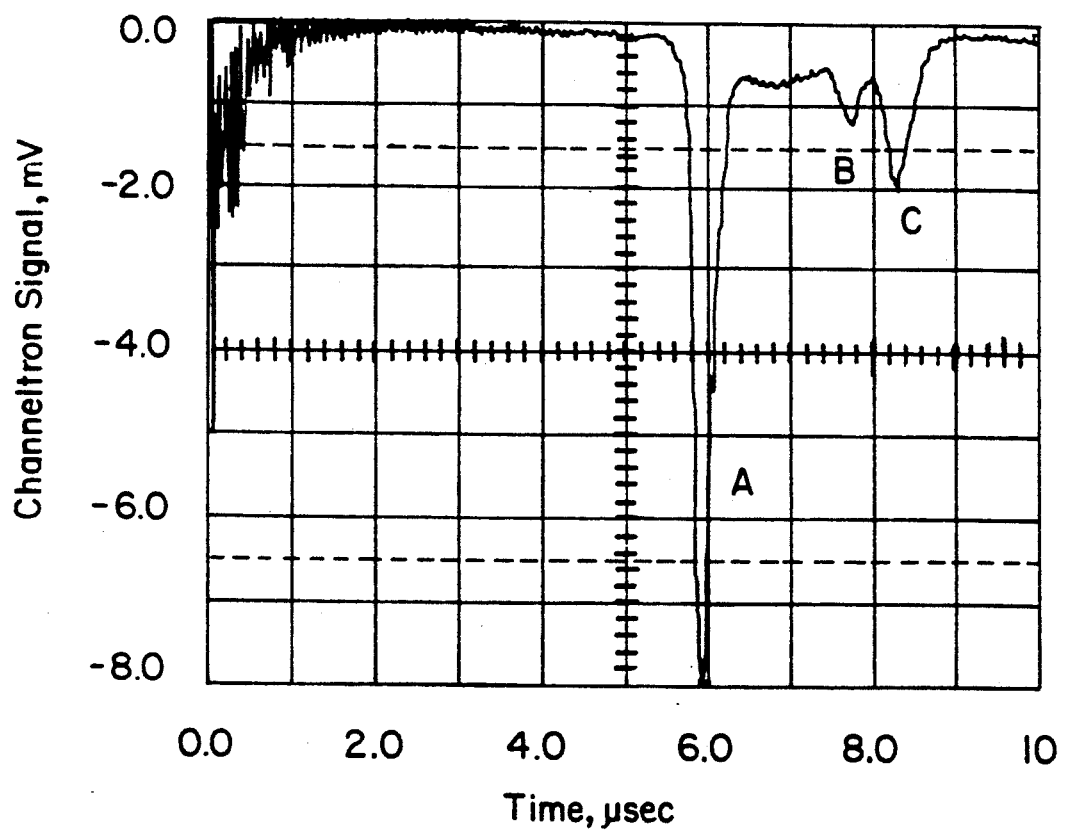
FIG. 8 is a spectrum of analyzed samples using the apparatus of FIGS. 6 and 7.

A sample of rhodamine labeled thyamine triphosphate is mixed at a 1 to 100 ratio into rhodamine 6-G dye. The sample was then spotted onto the sample holder as described previously. The vaporization laser 14 at 532 nm, was directed onto the sample thin film with a fluence of 40 mJ/cm$^2$. The ionization laser at 308 nm was maintained at 30 mJ/cm$^2$. A representative time-of-flight spectrum is shown in FIG. 8 which is prepared from the oscilloscope 86 connected to the Channeltron inputs 68 and the photodiode 82 via lines 88 and 90, respectively.

In this plot (FIG. 8), the current signal output from the Channeltron is plotted as a function of time in microseconds. The peak appearing at 5.9 microseconds, labeled A, has been identified as pure rhodamine 6-G (MW=479 AMU) by control experiments where no labeled DNA is present. In the same control experiment, it was determined that the peak at 8.3 microseconds, labeled C, also resulted from the rhodamine 6-G dye. The ratio of arrival times for these two peaks is precisely a factor of $2^{1/8}$. (Note that in a time of flight spectrum the time of arrival for an ion of a given mass scales as the square root of mass). This strongly suggests that the peak at 8.3 microseconds is the dimer of the rhodamine 6-G dye (MW=958 AMU).

When the rhodamine 6G labeled nucleotide sample is added to the thin film, the peak at 7.7 microseconds, labeled B, appears. This arrival time implies that a species of approximately 800 AMU is present in the vaporized sample. This is the equal to the mass we calculate for the tagged nucleotide.

Note that no other peaks in the mass spectrum are present at shorter or longer times suggesting that no fragmentation of the nucleotide or rhodamine 6-G occurs either during the vaporization or the ionization step.

VAPORIZATION OF AN OLIGONUCLEOTIDE

The aim of these experiments was to probe the experimental condition which resulted in molecular desorption from the sample thin film. To execute these experiments, all of the vaporized materials were trapped onto a piece of filter paper. This sample was then subjected to rigorous bioanalytical analysis for strand degradation.

In this experiment, the ion detection system of FIG. 6 is removed from the apparatus and a simple piece of filter paper is installed to collect all of the laser vaporization materials. A 4 mm diameter hole is placed in the filter paper to allow passage of the vaporization laser. The paper is positioned at a distance of 10 mm from the vaporization spot on the thin film.

An oligonucleotide (50 pmol) having the sequence 5'-GTTTTCCCAGTCACGAC-3' was synthesized, purified by HPLC, and labeled at the 5' end with $^{32}P$ using polynucleotide kinase. The final specific activity of the oligonucleotide was 300 (counts per minute) cpm/fmol. Five (PICO) pmol of the oligonucleotide was dissolved in 4 μl of water containing 10 mg/ml rhodamine 5G. This results in a final molar ratio of sample to dye of 1:17,000. This mixture was then spotted in two 2 μl aliquots on a glass cover slip. The dried sample was placed in the sample chamber, the chamber evacuated to $5 \times 10^{-6}$ torr, and then the sample was exposed to the second harmonic of the Nd YAD III laser (532 nm, 8 ns pulse length) at a power equal to 130 mJ/cm$^2$. The filter containing the putative vaporized DNA was removed and the process twice repeated on fresh samples at power levels equal to 85 and 45 mJ/cm$^2$.

Figure 9:
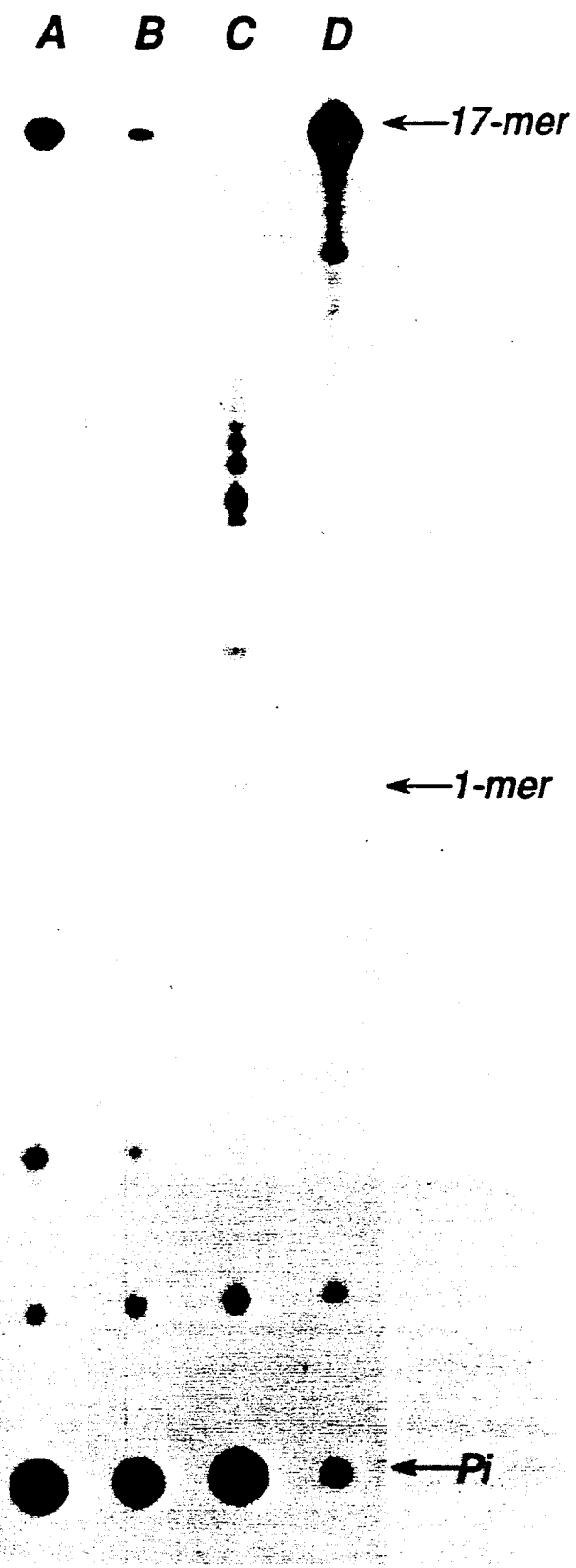
FIG. 9 is an autoradiograph showing a vaporized oligonucleotide.

The position of the $^{32}P$-labeled DNA on the filter papers was visualized by autoradiography. The radioactivity on the filters displayed an even distribution suggesting that the DNA had been, in fact, vaporized rather than spalled since spallation would have produced a spotted or flecked appearance on the filter, which has also been observed under different vaporization conditions. The radioactively labeled DNA was eluted from the label-containing region of each filter with two 150 μl portions of water, the resulting solutions concentrated in vacuo, and each sample loaded on a 20% acrylamide gel. The samples were electrophoresed for 3 h at 1000 volts and visualized by autoradiography (FIG. 9). Analysis showed that the sample vaporized with 130, 85 and 45 mJ/cm$^2$, (lanes A, B & C) respectively. Lane D contains an arbitrary amount of the starting 17-mer. It is clearly evident that at higher power levels (130 and 85 mJ/cm$^2$) no observable strand scission occured.

While the forms of the invention herein described constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

What is claimed is:

1. A method analyzing an organic sample, comprising the steps of:
    a) providing an organic sample in a medium which absorbs lights wherein the sample is a nucleic acid that has been fragmented such that each fragment terminates with one of the bases adenosine (A), cytosine (C), quanosine (G), or thymidine (T):
    b) vaporizing the sample and the medium into the gaseous state;
    c) inoizing the vaporized sample; and
    d) detecting the contents of the vaporized, ionized sample.

2. The method of claim 1 wherein the organic sample to be analyzed has an ionizable chromophore covalently bonded to the sample.

3. The method of claim 2 wherein the chromophore to be bonded to the sample is a dye.

4. The method of claim 2 wherein the chromophore to be bonded to the sample is a fluorescent dye.

5. The method of claim 2 wherein the chromophore to be bonded to the sample is selected from the group consisting of fluorescein, rhodamine, tetramethyl rhodamine, sulforhodamine, nitrobenzo-2-oxa-1-diazole and derivatives thereof which can covalently react with a biomolecule sample.

6. The method of claim 5 wherein the derivatives are selected from the group consisting of iodoacetamide, maleimide, isothiocyanate and succinimidyl carboxylate.

7. The method of claim 1 wherein the light absorbing medium is an organic dye.

8. The method of claim 1 wherein the light absorbing medium is in the liquid state.

9. The method of claim 1 wherein the light absorbing medium is in the solid state.

10. The method of claim 1 wherein the contents of the vaporized, ionized sample is determined by utilizing a mass spectrometer of the time-of-flight type.

11. The method of claim 1 wherein the sample is a protein.

12. The method of claim 1 wherein the vaporizing step is performed by a laser.

13. The method of claim 1 wherein the ionizing step is performed by a laser.

14. The method of claim 1 wherein the light absorbing medium has the ability to absorb light at a wavelength greater than 500 nanometers.

15. The method of claim 1 wherein the light absorbing medium is comprised of a dye.

16. The method of claim 1 wherein the amount of light absorbing medium used ranges from about 100 to about 100,000 parts by weight for each part of the sample in the light absorbing medium.

17. A method for determining the base sequence of a nucleic acid strand wherein four separate nucleic acid samples derived from the strand are fragmented such that each fragment in a particular sample terminates at one of the bases adenosine (A), cytosine (C), guanosine (G), or thymidine (T), comprising the steps of:

(a) providing an organic sample comprised of the four samples of the nucleic acid in a light absorbing medium which absorbs light;
(b) vaporizing the sample and the light absorbing medium into the gaseous state;
(c) ionizing the vaporized sample; and
(d) detecting the contents of the vaporized, ionized sample.

18. The method of claim 17 wherein the nucleic acid sample to be analyzed has an ionizable chromophore covalently bonded to the sample.

19. The method of claim 17 wherein the light absorbing medium is an organic dye.

20. The method of claim 17 wherein the light absorbing medium is in the liquid state.

21. The method of claim 17 wherein the light absorbing medium is in the solid state.

22. The method of claim 17 wherein the contents of the vaporized, ionized sample is determined by utilizing a mass spectrometer of the time-of-flight type.

23. The method of claim 17 wherein the vaporizing step is performed by a laser.

24. The method of claim 17 wherein the ionizing step is performed by a laser.

25. The method of claim 17 wherein the light absorbing medium has the ability to absorb light at a wave length less than 500 nanometers.

26. The method of claim 17 wherein the light absorbing medium is comprised of a dye.

27. The method of claim 17 wherein the chromophore to be bonded to the sample is a dye.

28. The method of claim 17 wherein the chromophore to be bonded to the sample is a fluorescent dye.

29. The method of claim 17 wherein the chromophore to be bonded to the sample is selected from the group consisting of fluorescein, rhodamine, tetramethyl rhodamine, sulforhodamine, nitrobenzo-2-oxa-1-diazole and derivatives thereof which can covalently react with a biomolecule sample.

30. The method of claim 17 wherein the derivatives are selected from the group consisting of iodoacetamide, maleimide, isothiocyanate and succinimidyl carboxylate.

31. The method of claim 17 wherein the amount of light absorbing medium used ranges from about 100 to about 100,000 parts by weight for each part of the sample in the light absorbing medium.

32. An apparatus that does analyze nucleic acid material present in a visible light absorbing medium comprising:

an optical source for generating electromagnetic radiation in the visible light region capable of vaporizing the nucleic acid sample material in the visible light absorbing medium which absorbs visible light;

a source of ionizing radiation capable of ionizing the vaporized sample; and an apparatus, juxtaposed to the vaporized, ionized sample, capable of determining the contents of the vaporized, ionized sample.

33. The apparatus of claim 32 further comprising a pulsed nozzle positioned between the sample and the output of the source of vaporizing energy which is timed to open in concert with the exposure of the sample to the electromagnetic radiation and capable of remaining open for a sufficient of period of time necessary to allow the vaporized sample to enter the ionizing chamber.

34. The apparatus of claim 32 wherein the apparatus that is capable of determining the contents of the vaporized, ionized sample is a Channeltron.

35. The apparatus of claim 34 wherein the apparatus capable of determining the contents of the vaporized ionized sample is a mass spectrometer.

36. The apparatus of claim 35 wherein the mass spectrometer is a time-of-flight type mass spectrometer.

37. The apparatus of claim 32 wherein the source of vaporizing radiation is a laser.

38. The apparatus of claim 32 wherein the source of ionizing radiation is a laser.

* * * * *

UNITED STATES PATENT AND TRADEMARK OFFICE
CERTIFICATE OF CORRECTION

PATENT NO. : 5,210,412
DATED : May 11, 1993
INVENTOR(S) : Robert J. Levis and Louis J. Romano It is certified that error appears in the above-indentified patent and that said Letters Patent is hereby corrected as shown below:

Column 2, Line 34                       after "Nos." insert
--4,855,255--.

Column 3, Line 23                       after "MASS"
replace "SEPCTROM" with --SPECTROM--.
Column 12, Line 65
replace "2178" with --21/2--.           after "factor of"

Column 14, Line 4
insert --,--.                           after "limiting"

Column 14, Line 14, Claim 1
          after "thymidine (T)" replace ":" with --;--.

Column 14, Line 17, Claim 1
          after "c)" replace "inoizing" with --ionizing--.

Signed and Sealed this

Twenty-second Day of March, 1994

Attest:

BRUCE LEHMAN

Attesting Officer        Commissioner of Patents and Trademarks